United States Patent [19]

Oi et al.

[11] Patent Number: 5,068,459

[45] Date of Patent: Nov. 26, 1991

[54] PROCESS FOR PRODUCING M-PHENOXYBENZYL ALCOHOL

[75] Inventors: Ryu Oi; Shinji Takenaka; Chitoshi Shimakawa, all of Omuta, Japan

[73] Assignee: Mitsui Toatsu Chemicals, Inc., Tokyo, Japan

[21] Appl. No.: 509,843

[22] Filed: Apr. 17, 1990

[30] Foreign Application Priority Data

Apr. 19, 1989 [JP] Japan ................................. 1-97630

[51] Int. Cl.$^5$ ............................................. C07C 41/01
[52] U.S. Cl. ..................................................... 568/638
[58] Field of Search ................ 568/637, 638, 639, 629

[56] References Cited

U.S. PATENT DOCUMENTS 4,694,110  9/1987  Takenaka et al. .................. 568/638

OTHER PUBLICATIONS

Morrison and Boyd, *Organic Chemistry*, 4th edition, (1983), pp. 457 and 993.

*Primary Examiner*—Alan Siegel
*Assistant Examiner*—Margaret Argo
*Attorney, Agent, or Firm*—Millen, White & Zelano

[57] ABSTRACT

A process for producing m-phenoxybenzyl alcohol by reacting chlorobenzene with m-hydroxybenzyl alcohol in the presence of a copper catalyst and a base, the process being characterized by using an alkylene glycol as a reaction solvent.

4 Claims, No Drawings

PROCESS FOR PRODUCING M-PHENOXYBENZYL ALCOHOL

The present invention relates to a process for producing m-phenoxybenzyl alcohol.

m-Phenoxybenzyl alcohol is a raw material for pyrethroid type insecticides. In recent years, demand for pyrethroid type agricultural chemicals of low toxicity has been high in view of the effect of agricultural chemicals on the human body; accordingly, supplying m-phenoxybenzyl alcohol at a low cost is an important task in the development of said agricultural chemicals.

For production of m-phenoxybenzyl alcohol, there have generally been known processes comprising subjecting m-phenoxytoluene to chlorination or oxidation. These processes, however, have the following drawbacks and therefore have been unsatisfactory in order to provide m-phenoxybenzyl alcohol of low cost advantageously in industry.

(1) Process comprising subjecting m-phenoxytoluene to side chain chlorination

In the chlorination reaction of side chain methyl group, there also occurs undesired chlorine addition at the benzyl-position and accordingly there is formed a by-product. As a result, the selectivity is lowered; an additional separation and purification is required; and the subsequent hydrolysis step becomes complex.

(2) Process comprising subjecting m-phenoxytoluene to side chain oxidation

In the oxidation of side chain methyl group, severe reaction conditions of high temperature and high pressure are required, and consequently the benzyl-position is oxidized not only to an alcohol but also to an aldehyde and/or a carboxylic acid. In order to obtain an intended product, the thus formed benzaldehyde and/or benzoic acid must be reduced; thus, the steps become complex as in the process (1).

For production of m-phenoxybenzyl alcohol, there is also known a process comprising condensing a m-chlorobenzoic acid ester or nitrile with a phenolate (French Patent No. 2456727). However, this process is not advantageous for use as an industrial process because the m-chlorobenzoic acid ester or nitrile is expensive.

For production of m-phenoxybenzyl alcohol, there is also proposed a process comprising condensing m-hydroxybenzyl alcohol with bromobenzene in the presence of a copper catalyst to obtain m-phenoxybenzyl alcohol Japanese Laid-Open Patent Publications Nos. 61443/1973 and 186339/1986). However, this process is insufficient for use as an industrial process because bromobenzene is expensive.

The present inventors had previously succeeded in producing m-hydroxybenzyl alcohol from m-hydroxybenzoic acid at a relatively low cost. Further, the present inventors studied on a process for producing m-phenoxybenzyl alcohol from the above-obtained m-hydroxybenzyl alcohol and chlorobenzene and found out a process for producing m-phenoxybenzyl alcohol at a high yield (U.S. Pat. No. 4,694,110 and Japanese Laid-Open Patent Publication No. 41435/1988).

In this process, m-phenoxybenzyl alcohol is produced by reacting m-hydroxybenzyl alcohol with chlorobenzene at 140°–200° C. in the presence of a catalyst (an 8-oxyquinoline copper complex) and a base in a polar solvent (e.g., N,N'-dimethylimidazolidinone, N,N'-dimethylformamide, dimethyl sulfoxide, N-methyl-2-pyrrolidone or sulfolane) while removing the formed water under azeotropy with chlorobenzene.

The process has an advantage of being able to provide intended m-phenoxybenzyl alcohol at a high yield. However, the process has various drawbacks as follows. The polar solvent used is relatively expensive and, therefore, in order to carry out the process in industry, there must be established an additional procedure for filtering the reaction mixture to remove the insoluble inorganic salt, subjecting the filtrate to distillation to recover the polar solvent together with chlorobenzene, and reusing the recovered polar solvent; moreover, since the polar solvent is relatively unstable under a basic condition and is partially decomposed during the reaction, to form a tar-like substance, the filtrability of the reaction mixture to remove the inorganic salt is low and consequently the recoverability of the polar solvent by subjecting the filtrate to distillation is poor.

Thus, in order to develop the condensation reaction of m-hydroxybenzyl alcohol with chlorobenzene into an industrially feasible process for producing m-phenoxybenzyl alcohol, it is necessary that not only the yield of intended m-phenoxybenzyl alcohol be increased but also the cost of the solvent in the total production cost be lowered.

Hence, the object of the present invention is to produce an industrially feasible process for producing m-phenoxybenzyl alcohol, by using a reaction solvent which is inexpensive, is stable under a basic condition and low in decomposition tendency (accordingly produces only a small amount of a tar-like substance), makes easy the post-treatment (filtration) and can be recovered at a high efficiency.

As a result of extensive study, the present inventors have found that when an alkylene glycol is used as a reaction solvent, m-phenoxybenzyl alcohol can be obtained at a high yield, the alkylene glycol is stable under the basic reaction condition of the present invention and forms no tar, the filtration after the reaction is improved, and the recoverability of the solvent is improved.

According to the present invention, there is provided a process for producing m-phenoxybenzyl alcohol by reacting chlorobenzene with m-hydroxybenzyl alcohol in the presence of a copper catalyst and a base, the process being characterized by using an alkylene glycol as a reaction solvent.

Chlorobenzene, which is one raw material in the present process, is produced by chlorination of benzene, in a large amount in industry and is easily available.

m-Hydroxybenzyl alcohol, which is another raw material in the present process, is synthesized by, for example:

a fermentation method using m-cresol as a raw material, a method of reducing m-hydroxybenzaldehyde, or a method of reducing m-hydroxybenzoic acid.

The base used in the present process is no particularly restricted and includes, for example, a sodium or potassium alcoholate (e.g. sodium ethoxide, sodium ethoxide, potassium tert-butoxide), sodium hydroxide, potassium hydroxide, sodium carbonate, potassium carbonate, sodium hydrogencarbonate and potassium hydrogencarbonate. The amount of the base used must be at least stoichiometric to the amount of m-hydroxybenzyl alcohol and is ordinarily 1.0–4.0 moles, preferably 1.0–2.0 moles, per mole of m-hydroxybenzyl alcohol. When the amount is more than the upper limit of the above range, there is seen no further improvement in reaction rate, etc. and there tends to be formed an increased amount of a by-product, i.e. m-phenoxybenzyl phenyl ether which is a reaction product of m-phenoxybenzyl alcohol intended product) and chlorobenzene.

Depending upon the type of the base used, water is formed by the reaction of m-hydroxybenzyl alcohol and the base. Therefore, it is preferable to remove the water in the initial reaction or during the reaction, under azeotropy with chlorobenzene.

The reaction solvent usable in the present process is an alkylene glycol. The alkylene glycol is preferably one represented by the formula

$$R'-O\!\!+\!\!CHCHO\!\!+\!\!_n R \qquad (I)$$

wherein R and R' are independently a hydrogen atom, a methyl group, an ethyl group, a propyl group or a butyl group, $X_1$ and $X_2$ are independently a hydrogen atom or a methyl group, and n is an integer of 1–10. As specific examples of the alkylene glycol, there can be mentioned glycols such as ethylene glycol, diethylene glycol, triethylene glycol, tetraethylene glycol, propylene glycol, dipropylene glycol, tripropylene glycol and the like; monoethers of said glycols such as glycol monomethyl ether, glycol monoethyl ether, glycol monopropyl ether, glycol monoisopropyl ether, glycol mono-n-butyl ether, glycol monoisobutyl ether and the like; diethers of said glycols such as glycol dimethyl ether, glycol diethyl ether, glycol dipropyl ether, glycol diisopropyl ether, glycol di-n-butyl ether, glycol diisobutyl ether and the like. These alkylene glycols as a reaction solvent can be used alone or in admixture of two or more. It is possible to use such an alkylene glycol in combination with an aprotic polar solvent.

The amount of the reaction solvent used must be at least 0.1 mole per mole of m-hydroxybenzyl alcohol in order for the solvent to exhibit its effect. However, the amount is ordinarily 0.1–10.0 moles, preferably 0.3–5.0 moles, because too large an amount reduces the volumetric efficiency of the reaction.

The amount of chlorobenzene used must be at least equivalent to m-hydroxybenzyl alcohol, but is ordinarily 1.0–20.0 moles, preferably 2.0–10.0 moles, per mole of m-hydroxybenzyl alcohol because too large an amount reduces the volumetric efficiency of the reaction.

As the copper catalyst used in the present process, there can be illustrated a copper powder, copper chloride, copper carbonate, etc. They may be used as such but are used preferably in the form of a complex, for example, 8-oxyquinoline copper complex disclosed in Japanese Laid-Open Patent Publication No. 134743/1874. The 8-oxyquinoline copper complex can be used in an amount of ordinarily 0.5–5.0 mole % relative to m-hydroxybenzyl alcohol.

In the present process, the reaction temperature is ordinarily 120°–200° C., preferably 130°–170° C., more preferably 150°–170° C. When the reaction temperature is lower than 120° C., the reaction rate is extremely low. When the reaction temperature is higher than 200° C., m-hydroxybenzyl alcohol as a raw material causes thermal decomposition and the selectivity of m-phenoxybenzyl alcohol is low.

The reaction pressure may be atmospheric but, in order to obtain a high reaction rate, is preferably about 0.5–5.0 kg/cm².

The reaction time differs by the reaction temperature and/or the reaction pressure, but generally is about 10–30 hours under the atmospheric pressure and about 1–10 hours under applied pressure.

The reaction is usually effected preferably in an inert gas atmosphere such as nitrogen gas or the like, in order to avoid, for example, the oxidation reaction of m-phenoxybenzyl alcohol which is an intended product.

The excessive chlorobenzene and the alkylene glycol, both of which remain in the reaction mixture after the completion of the reaction, can be removed by filtering the reaction mixture to remove the insoluble inorganic salt and the catalyst and then subjecting the filtrate to distillation. When the recovery of the alkylene glycol is unnecessary, the reaction mixture is water washed after the completion of the reaction, the aqueous layer containing the alkylene glycol is discarded, the organic layer is subjected to distillation to recover chlorobenzene and obtain pure m-phenoxybenzyl alcohol.

The present invention is hereinafter described specifically by way of non-limitative Examples.

EXAMPLE 1

Into a reactor provided with a reflux condenser and a dehydrating tube were charged 50.0 g (0.40 mole) of m-hydroxybenzyl alcohol, 90.0 g (0.80 mole) of chlorobenzene, 164.2 g (1.00 mole) of triethylene glycol monomethyl ether, 41.8 g (0.30 mole) of potassium carbonate, 0.8 g of cuprous chloride and 1.2 g of 8-oxyquinoline.

The mixture was heated to 150° C. in a nitrogen gas atmosphere, and stirred at that temperature for 20 hours while effecting refluxing and dehydration.

After the completion of the reaction, the reaction mixture was cooled to 70° C. and filtered under reduced pressure [filter paper used: filter paper No. 3 dia.: 60 mm) for Kiriyama funnel, vacuum: 20–30 mmHg]. The time required for filtering was about 3 minutes.

The insoluble inorganic substances were removed by the above filtration. The filtration residue was washed with a small amount of chlorobenzene and the washings were added to the filtrate.

This combined solution was subjected to GLC analysis. The analysis indicated that the conversion of m-hydroxybenzyl alcohol was 99%, the yield of m-phenoxybenzyl alcohol was 93%, and the residue percentage of triethylene glycol monomethyl ether was 98% relative to the charged amount.

The combined solution was also subjected to vacuum distillation, and there were recovered chlorobenzene and 162.5 g (purity: 98%, recovery: 97%) of triethylene glycol monomethyl ether, and there was obtained 71.6 g purity: 98%, isolation yield: 87%) of pure m-phenoxybenzyl alcohol.

EXAMPLE 2

In an autoclave provided with a reflux condenser and a dehydrating tube were charged 20.0 g (0.16 mole) of m-hydroxybenzyl alcohol, 70.5 g (0.63 mole) of chlorobenzene, 19.2 g (0.16 mole) of diethylene glycol monomethyl ether, 16.7 g (0.12 mole) of potassium carbonate, 0.40 g of cupric chloride and 0.48 g of 8-oxyquinoline. oxyquinoline.

The autoclave inside was purged with nitrogen gas and heated to 160° C., and stirring was effected at that temperature for 4 hours. The reaction pressure was 1.3-1.7 kg/cm².

After the completion of the reaction, the reaction mixture was cooled to 70° C., and the same post-treatment as in Example 1 was effected. The filtration was complete within 3 minutes.

There were recovered chlorobenzene and 18.8 g (purity: 98%, recovery: 96%) of diethylene glycol monomethyl ether, and there was obtained 28.6 g (purity: 97%, isolation yield: 86%) of pure m-phenoxybenzyl alcohol.

EXAMPLE 3

There were effected the same reaction and post-treatment as in Example 2 except that the diethylene glycol monomethyl ether was replaced by 30.0 g (0.20 mole) of diethylene glycol monoisopropyl ether. The filtration time was within 3 minutes.

There were recovered chlorobenzene and 30.0 g (purity: 95%, recovery: 95%) of diethylene glycol monoisopropyl ether, and there was obtained 28.3 g (purity: 97%, isolation yield: 85%) of pure m-phenoxybenzyl alcohol.

EXAMPLE 4

There were effected the same reaction and post-treatment as in Example 2 except that the amount of chlorobenzene used was increased to 143.9 g (1.28 moles) and the diethylene glycol monomethyl ether was replaced by 142.4 g (0.80 mole) of triethylene glycol monomethyl ether. The filtration time was within 3 minutes.

There were recovered chlorobenzene and 140.9 g purity: 98%, recovery: 97%) of triethylene glycol dimethyl ether, and there was obtained 27.8 g (purity: 98%, isolation yield: 85%) of pure m-phenoxybenzyl alcohol.

EXAMPLE 5

There were effected the same reaction and post-treatment as in Example 2 except that the diethylene glycol monomethyl ether was replaced by 39.6 g (0.3 mole) of propylene glycol mono-n-butyl ether. The filtration time was within 3 minutes.

There were recovered chlorobenzene and 38.8 g (purity: 98%, recovery: 96%) of propylene glycol mono-n-butyl ether, and there was obtained 28.1 g (purity: 98%, isolation yield: 86%) of pure m-phenoxybenzyl alcohol.

EXAMPLE 6

There were effected the same reaction and post-treatment as in Example 1 except that the diethylene glycol monomethyl ether was replaced by 17.0 g (0.16 mole) of diethylene glycol.

There were recovered, by vacuum distillation, chlorobenzene and 16.5 g (purity: 98%, recovery: 95%) of diethylene glycol, and there was obtained 12.6 g (purity: 97%, conversion: 44.8%, selectivity: 96%, isolation yield: 85%) of pure m-phenoxybenzyl alcohol.

EXAMPLE 7

There were effected the same reaction and post-treatment as in Example 1 except that the diethylene glycol monomethyl ether was replaced by 21.5 g (0.16 mole) of diethylene glycol dimethyl ether.

There were recovered, by vacuum distillation, chlorobenzene and 20.8 g (purity: 98%, recovery: 95%) of diethylene glycol dimethyl ether, and there was obtained 11.9 g (purity: 98%, conversion: 42%, selectivity: 95%, isolation yield: 86%) of pure m-phenoxybenzyl alcohol.

EXAMPLE 8

There were effected the same reaction as in Example 1 except that the diethylene glycol monomethyl ether was replaced by 10.0 g (0.05 mole) of polyethylene glycol (average moleculae weight: 200).

After the completion of the reaction, the reaction mixture was washed twice with water of a weight two times that of the reaction mixture to remove the polyethylene glycol into the aqueous layer. The organic layer was subjected to distillation to recover chlorobenzene and obtain 28.0 g (purity: 98%, isolation yield: 85%) of pure m-phenoxybenzyl alcohol.

COMPARATIVE EXAMPLE 1

There was effected the same reaction as in Example 1 except that the triethylene glycol monomethyl ether was replaced by 156.6 g (1.37 mole) of N,N'-dimethylimidazolidinone. After the completion of the reaction, the reaction mixture was cooled to 70° C. and subjected to the same vacuum filtration as in Example 1. The filtration time was 1 hour.

After the insoluble inorganic substances had been removed, the filtration residue was washed with a small amount of chlorobenzene, and the washings were combined with the filtrate. The combined solution was subjected to GLC analysis. The analysis indicated that the conversion of m-hydroxybenzyl alcohol was 98%, the yield of m-phenoxybenzyl alcohol was 90%, and the residue percentage of N,N'-dimethylimidazolidinone was 86% relative to the charged amount.

The combined solution was also subjected to vacuum distillation. As a result, there were recovered chlorobenzene and 134.0 g (purity: 97%, recovery: 83%) of N,N'-dimethylimidazolidinone, and there was obtained 70.7 g (purity: 97%, isolation yield: 85%) of pure m-phenoxybenzyl alcohol.

COMPARATIVE EXAMPLE 2

There was effected the same reaction and post-treatment as in Example 2 except that the diethylene glycol monomethyl ether was replaced by 23.4 g (0.30 mole) of dimethyl sulfoxide. The filtration time was 2 hours. There were recovered chlorobenzene and 18.1 g (purity: 97%, recovery: 75%) of dimethyl sulfoxide, and there was obtained 26.6 g (purity: 97%, isolation yield: 80%) of pure m-phenoxybenzyl alcohol.

COMPARATIVE EXAMPLE 3

There was effected the same reaction as in Example 2 that no diethylene glycol monomethyl ether was used, the amount of chlorobenzene used was increased to 90.0 g and the reaction time was 10 hours. The reaction mixture was subjected to GLC analysis, which indicated that the conversion of m-hydroxybenzyl alcohol was 75% and the yield of m-phenoxybenzyl alcohol was 51%.

As is clear from the data shown in the above Examples and Comparative Examples, when m-phenoxybenzyl alcohol is produced by the reaction of chlorobenzene with m-hydroxybenzyl alcohol in the presence of a copper catalyst and a base, using, as a reaction solvent, an alkylene glycol according to the present invention, there can be obtained various advantages such as:
the yield of m-phenoxybenzyl alcohol is good, the alkylene glycol is stable under a basic reaction condition and gives only a small amount of a tar-like decomposition product, and accordingly the filtration operation in the post-treatment is simple, and the recovery efficiency of the alkylene glycol is good and accordingly the solvent cost can be reduced significantly.

What is claimed is:

1. In a process for producing m-phenoxybenzyl alcohol by reacting chlorobenzene with m-hydroxybenzyl alcohol in a reaction solvent and in the presence of a copper catalyst and a base, the improvement which comprises using an alkylene glycol of the formula

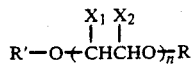

wherein R and R' are independently a hydrogen atom, a methyl group, an ethyl group, a propyl group or a butyl group, $X_1$ and $X_2$ are independently a hydrogen atom or a methyl group, and n is an integer of 1-10 as the reaction solvent.

2. The process set forth in claim 1, wherein the alkylene glycol is used in an amount of 0.1-10 moles per mole of m-hydroxybenzyl alcohol.

3. The process set forth in claim 1, wherein chlorobenzene is used in an amount of 1.0-20 moles per mole of m-hydroxybenzyl alcohol.

4. The process set forth in claim 1, wherein the reaction is conducted at 120°-200° C.

* * * * *